United States Patent
Stankus et al.

(10) Patent No.: US 9,220,819 B2
(45) Date of Patent: Dec. 29, 2015

(54) CROSS-LINKED COATING DELIVERED BY A BALLOON

(71) Applicant: ABBOTT CARDIOVASCULAR SYSTEMS INC., Santa Clara, CA (US)

(72) Inventors: John Stankus, Campbell, CA (US); Mikael Trollsas, San Jose, CA (US); Syed Hossainy, Hayward, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 246 days.

(21) Appl. No.: 13/842,314

(22) Filed: Mar. 15, 2013

(65) Prior Publication Data

US 2014/0277344 A1    Sep. 18, 2014

(51) Int. Cl.
| | |
|---|---|
| *A61F 2/00* | (2006.01) |
| *A61L 31/16* | (2006.01) |
| *A61M 25/10* | (2013.01) |
| *A61L 31/10* | (2006.01) |
| *A61F 2/82* | (2013.01) |

(52) U.S. Cl.
CPC .................. *A61L 31/16* (2013.01); *A61L 31/10* (2013.01); *A61M 25/10* (2013.01); *A61M 25/1006* (2013.01); *A61F 2/82* (2013.01); *A61F 2250/0067* (2013.01); *A61M 2025/105* (2013.01); *A61M 2025/1013* (2013.01); *A61M 2025/1075* (2013.01)

(58) Field of Classification Search
None
See application file for complete search history.

(56) References Cited

U.S. PATENT DOCUMENTS

| | | |
|---|---|---|
| 5,102,402 A | 4/1992 | Dror et al. |
| 6,129,705 A | 10/2000 | Grantz et al. |
| 6,406,457 B1 | 6/2002 | Wang et al. |
| 6,500,148 B1 | 12/2002 | Pinchuk et al. |
| 6,991,617 B2 | 1/2006 | Hektner et al. |
| 7,273,417 B1 | 9/2007 | Lundquist |
| 2008/0113081 A1 | 5/2008 | Hossainy et al. |
| 2011/0143014 A1* | 6/2011 | Stankus et al. ............... 427/2.14 |

OTHER PUBLICATIONS

Unverdoben, Martin, "The Paclitaxel-Eluting PTCA-Balloon Catheter in Coronary Artery Disease PEPCAD I-SVD PEPCAD II-ISR", Clinical Research Institute, Center for Cardiovascular Diseases, 2005-2006, Rotenburg/Fulda, Germany.

* cited by examiner

*Primary Examiner* — Susan Tran
(74) *Attorney, Agent, or Firm* — Baker Botts L.L.P.

(57) ABSTRACT

The present invention relates to systems for and corresponding methods of delivering a therapeutic agent to a vessel wall of a body lumen by providing a compound capable of being crosslinked after intraluminal release onto a vessel wall so that the therapeutic agent is temporarily retained at the site of delivery by the crosslinked compound.

10 Claims, 3 Drawing Sheets

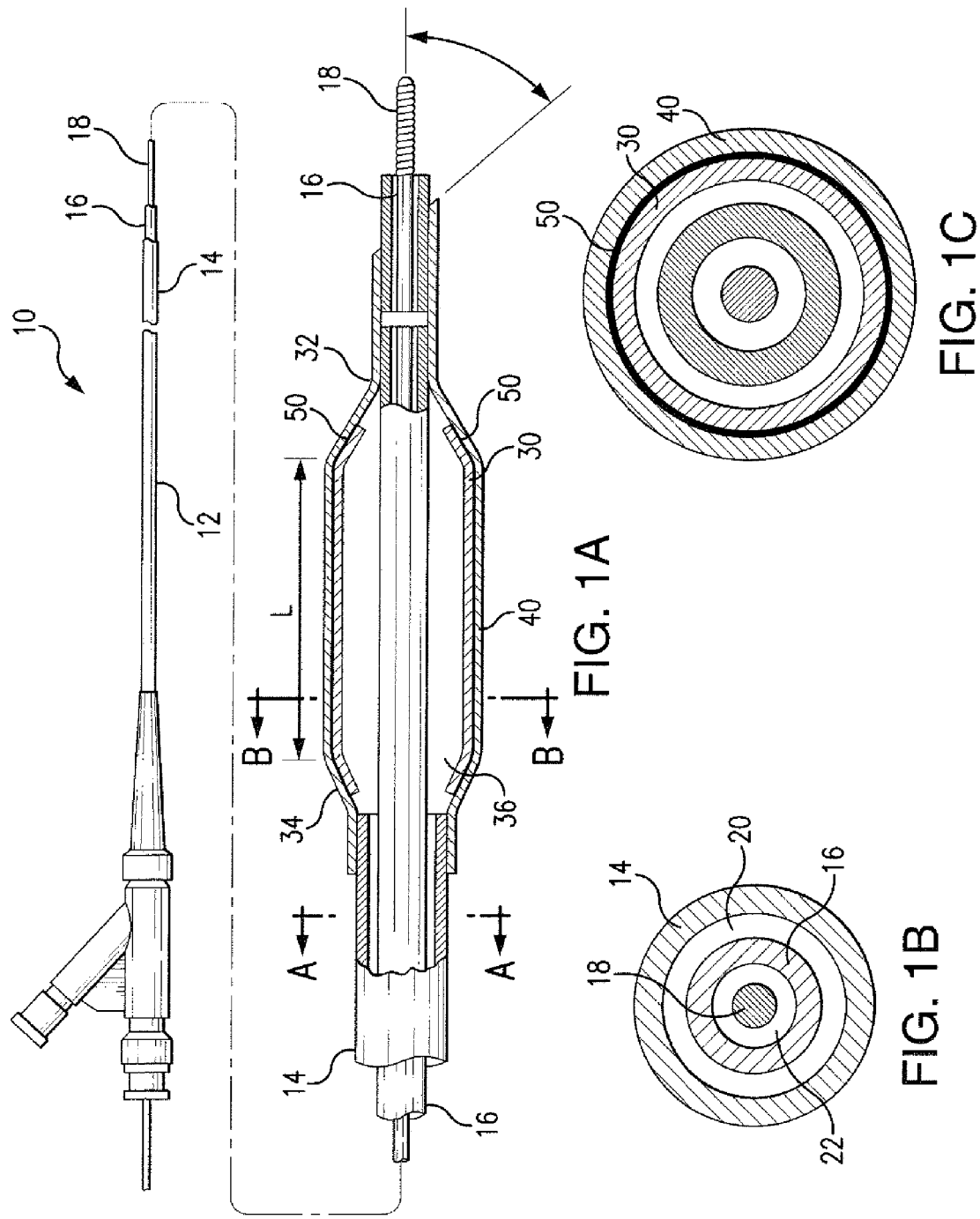

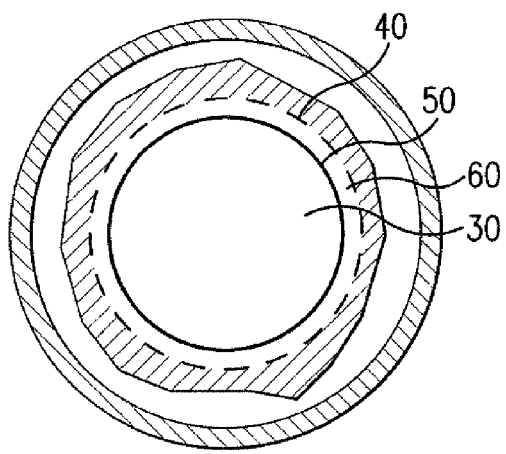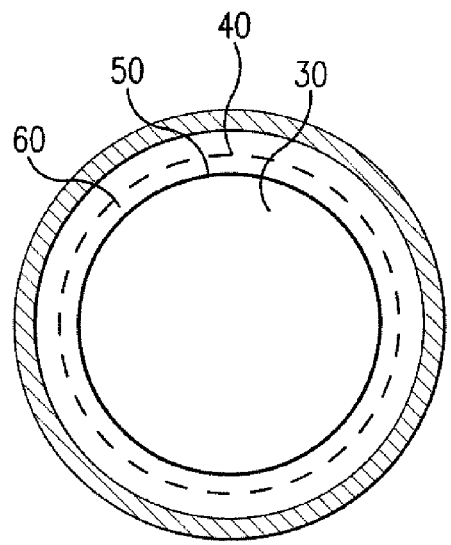
FIG. 3A          FIG. 3B
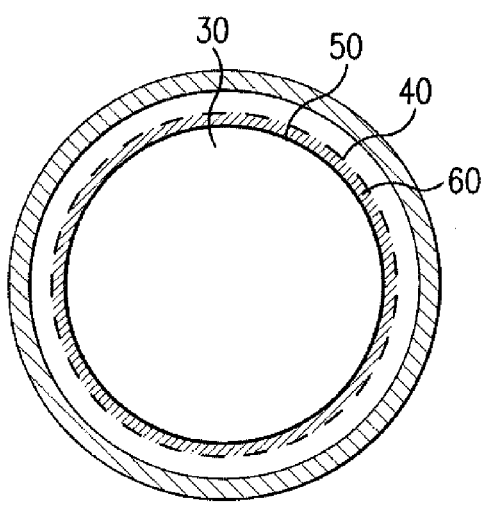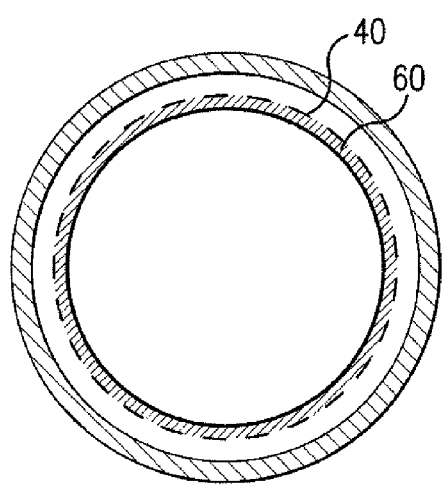
FIG. 3C          FIG. 3D

CROSS-LINKED COATING DELIVERED BY A BALLOON

FIELD OF THE INVENTION

The presently disclosed subject matter is related to the delivery of therapeutic agents from an interventional medical device. More particularly, the presently disclosed subject matter relates to delivery of therapeutic agents from an expandable member, such as a balloon, using a crosslinkable compound capable of being crosslinked on a vessel wall.

BACKGROUND OF THE INVENTION

Atherosclerosis is a syndrome affecting arterial blood vessels. It leads to a chronic inflammatory response in the walls of arteries, which is in large part due to the accumulation of lipid, macrophages, foam cells and the formation of plaque in the arterial wall. Atherosclerosis is commonly referred to as hardening of the arteries although the pathophysiology of the disease manifests itself with several different types of lesions ranging from fibrotic to lipid laden to calcific. Angioplasty is a vascular interventional technique involving mechanically widening an obstructed blood vessel, typically caused by atherosclerosis.

During angioplasty, a catheter having a tightly folded balloon is inserted into the vasculature of the patient and is passed to the narrowed location of the blood vessel at which point the balloon is inflated to a fixed size using an inflation fluid, typically a solution of angiographic contrast media. Percutaneous coronary intervention (PCI), commonly known as coronary angioplasty, is a therapeutic procedure to treat the stenotic coronary arteries of the heart, often found in coronary heart disease.

In contrast, peripheral angioplasty, commonly known as percutaneous transluminal angioplasty (PTA), refers to the use of mechanical widening of blood vessels other than the coronary arteries. PTA is most commonly used to treat narrowing of the arteries of the leg, especially, the iliac, external iliac, superficial femoral and popliteal arteries. PTA can also treat narrowing of veins and other blood vessels.

It was determined that following angioplasty, although a blood vessel would be successfully widened, sometimes the treated wall of the blood vessel experienced abrupt closure after balloon inflation or dilatation, due to acute recoil or spasm. Interventional cardiologists addressed this problem by stenting the blood vessel to prevent acute recoil and vasospasm. A stent is a device, typically a metal tube or scaffold, which was inserted into the blood vessel following angioplasty, in order to hold the blood vessel open.

While the advent of stents eliminated many of the complications of abrupt vessel closure after angioplasty procedures, within about six months of stenting, a re-narrowing of the blood vessel can form, which is a condition known as restenosis. Restenosis was discovered to be a response to the injury of the angioplasty procedure and is characterized by a growth of smooth muscle cells—analogous to a scar forming over an injury. As a solution, drug eluting stents were developed to address the reoccurrence of the narrowing of blood vessels. One example of a drug eluting stent is a metal stent that has been coated with a drug that is known to interfere with the process of restenosis. A potential drawback of certain drug eluting stents is known as late stent thrombosis, which is an event in which blood clots form inside the stent.

Drug coated balloons are believed to be a viable alternative to drug eluting stents in the treatment of atherosclerosis. In a study which evaluated restenosis, and the rate of major adverse cardiac events such as heart attack, bypass, repeat stenosis, or death in patients treated with drug coated balloons and drug eluting stents, the patients treated with drug coated balloons experienced only 3.7 percent restenosis and 4.8% MACE as compared to patients treated with drug eluting stents, in which restenosis was 20.8 percent and 22.0 percent MACE rate. (See, PEPCAD II study, Rotenburg, Germany).

Although drug coated balloons are a viable alternative and in some cases may have greater efficacy than drug eluting stents as suggested by the PEPCAD II study, drug coated balloons present challenges due to the very short period of contact between the drug coated balloon surface and the blood vessel wall. The drug delivery time period for a drug coated balloon differs from that of a controlled release drug eluting stent, which is typically weeks to months. In particular for the coronary arteries, the balloon may only be inflated for less than one minute, and is often inflated for only thirty seconds. Therefore, an efficacious, therapeutic amount of drug must be transferred to the vessel wall within a thirty-second to one-minute time period. For the peripheral vasculature, the allowable inflation times can be greater than one minute, but are still measured in minutes. Thus, there are challenges specific to drug delivery via a drug coated balloon because of the necessity of a short inflation time, and therefore time for drug or coating transfer—a challenge not presented by a drug eluting stent, which remains in the patient's vasculature once implanted.

Various embodiments of drug-coated balloons have been proposed to address these needs, including balloons with a therapeutic agent disposed directly on the balloon surface and balloons having various protective sheaths. However, not all embodiments result in an efficacious response in reducing restenosis after balloon and/or bare metal stent trauma.

Furthermore, it is desirable to retain the drug on the vessel wall after balloon inflation and release of the coating to the site of delivery. Tissue retention will depend on several factors, including characteristics of the therapeutic agent and the formulation of the balloon coating. Such retention will permit greater local drug uptake, thereby improving treatment efficacy and decreasing systemic exposure to the therapeutic agent.

Thus, there remains a need for, and an aim of the disclosed subject matter is directed towards, coating compositions and corresponding methods for drug delivery balloons that permit enhanced retention of the coating at the site of delivery by chemical modification of the coating at the delivery site.

SUMMARY OF THE INVENTION

The purposes and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims herein, as well as from the appended drawings.

To achieve these and other advantages and in accordance with the purpose of the disclosed subject matter, as embodied and broadly described, the disclosed subject matter includes systems and methods for delivery of a therapeutic agent to a vessel wall of a body lumen. In accordance with the disclosed subject matter, a system includes an expandable member having a distal end, a proximal end and a working length therebetween, a crosslinkable compound capable of being crosslinked after intraluminal release onto a vessel wall disposed along at least a portion of the working length, and at least one therapeutic agent disposed along the portion of the working length so as to be temporarily retained by the crosslinkable compound after intraluminal release to the vessel wall.

In some embodiments of the disclosed subject matter, the therapeutic agent is selected from the group consisting of antithrombotics, anticoagulants, antiplatelet agents, antilipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, cytostatic drugs, antimitotics, antifibrins, antioxidants, antineoplastics, agents that promote endothelial cell recovery, antiallergic substances, viral vectors, nucleic acids, monoclonal antibodies, antisense compounds, oligonucleotides, cell permeation enhancers, radiopaque agent markers, HMG CoA reductase inhibitors, pro-drugs, and combinations thereof.

According to one aspect of the disclosed subject matter, the crosslinkable compound can be disposed as a coating on the expandable member, such as an outer layer containing a therapeutic agent or agents. Additionally or alternatively, the expandable member can have an outer surface with reservoirs containing the crosslinkable compound for intraluminal release. Alternatively or concomitantly, the expandable member can have pores along the portion of the working length, such that the crosslinkable compound is released through the pores. The therapeutic agent or agents can also be located within the reservoirs or pores for intraluminal release upon inflation.

In certain embodiments, the crosslinkable compound is crosslinked by thermal treatment. The compound can crosslink at a temperature of 37 degrees Celsius or above. Compounds of such embodiments can be selected from the group consisting of silk-elastin-like protein-based polymers, pluronics F127, pluronics F68, poly N-isopropylacrylamide ("polyNIPAAM"), polyNIPAAM-co-acrylic acid, PEG-PEG-PLA-PEG, PLGA-PEG, PLGA, solubilized extracellular matrix, self-assembling peptides, hydroxypropylmethylcellulose, or a combination thereof. A heat source can also be provided with the system of these embodiments to heat the compound on the vessel wall to a temperature above 37 degrees Celsius after intraluminal delivery.

In other embodiments of the present invention, the crosslinkable compound is crosslinked by melt thermal treatment. The crosslinkable compound of such embodiments can crosslink at or below about 37 degrees Celsius. Compounds of these embodiments can be selected from the group consisting of poly($\epsilon$-caprolactone), poly(ortho esters) and polyanhydrides. A heat source can be provided with the system of these embodiments to heat the compound to a temperature above 37 degrees Celsius for intraluminal release from the balloon, and subsequent cooling and crosslinking on the vessel wall.

In other embodiments, the crosslinkable compound of the present invention is crosslinked by solvation. Compounds of these embodiments can be selected from the group consisting of poly(ester amide), poly(lactic-co-glycolic acid) ("PLGA"), poly-DL-lactide ("PDLLA"), poly-L-lactide ("PLLA"), PLGA-polyethylene glycol ("PEG")-PLGA, PLLA-PEG-PLLA, and a combination thereof. Suitable solvents for these embodiments include N-methylpyrrolidinone, dimethyl sulfoxide, and dichloromethane. In this embodiment, the solvent and the crosslinkable compound can be delivered independently along the working length of the expandable member, for example in the reservoirs described above and applied as a coating respectively, and combined at the site of delivery.

In other embodiments of the disclosed subject matter, the crosslinkable compound is shear-sensitive so as to crosslink upon removal of shear associated with inflation at the site of delivery and/or intraluminal release to the vessel wall. Crosslinkable compounds of these embodiments can be selected from the group consisting of sodium hyaluronate, sodium alginate, and certain lightly crosslinked hydrogels such as lightly crosslinked sodium alginate, lightly crosslinked sodium hyaluronate/methylcellulose blends, or a combination thereof.

For certain other embodiments, a crosslinkable compound is provided capable of crosslinking within a pH range of between about 6.8 and about 7.4. Crosslinkable compounds of these embodiments can be selected from the group consisting of acid-soluble collagen, chitosan, polyacrylic acid, or a combination thereof.

In other embodiments of the disclosed subject matter, the crosslinkable compound is crosslinked by chemical reaction with a second compound. The second compound is disposed along at least a portion of the working length of the expandable member. Crosslinkable compounds of these embodiments can be selected from the group consisting of PEG N-hydroxysuccinamide ("NHS") ester, PEG acrylate, PEG amine, PEG thiol, sodium hyaluronate acrylate, hyaluronate thiol, fibrin, and methacrylate modified acrylate. The compounds of these embodiments can be selected so as to be chemically reactive in an environment having a predetermined pH range. In one aspect, the predetermined pH is at least about 6.8.

In other embodiments of the disclosed subject matter, the crosslinkable compound is crosslinked by photoactivation. Crosslinkable compounds of these embodiments can be selected from the group consisting of 2-hydroxy-1[4-(hydroxyethoxy)phenyl]-2-methyl-1-propanone, PEG acrylate, methacrylate modified alginate, methacrylate modified hyaluronan, and a combination thereof. The system of such embodiments can include a light source to crosslink the compound by photoactivation. A second compound crosslinkable by photoactivation can also be disposed along the working length of the expandable member.

In yet other embodiments, the crosslinkable compound can be crosslinked by ionic crosslinking. Suitable crosslinkable compounds can be selected from the group consisting of sodium alginate, pectin, aloe pectin, and a combination thereof. A second compound optionally can be disposed on at least a portion of the working length of the expandable member, wherein the second compound is selected from the group consisting of calcium chloride, barium chloride, and a combination thereof. In this manner, the second compound dissociates into corresponding component ions to crosslink the crosslinkable compound at the site of delivery.

Additionally, the disclosed subject matter includes a method of delivering a therapeutic agent to a vessel wall of a body lumen. The method includes providing a system corresponding to an embodiment described above, positioning the expandable member in a body lumen, expanding the expandable member to contact the vessel wall for intraluminal release of the crosslinkable compound onto the vessel wall, and crosslinking the crosslinkable compound on the vessel wall such that the therapeutic agent or agents are temporarily retained by the crosslinked compound at the vessel wall.

BRIEF DESCRIPTION OF THE DRAWINGS

FIG. 1A is a schematic view of one representative balloon catheter in accordance with the disclosed subject matter. FIG. 1B is a schematic cross-sectional end view taken along lines A-A in FIG. 1A. FIG. 1C is a schematic cross-sectional end view taken along lines B-B in FIG. 1A.

FIG. 2 is a schematic side view representation of the disclosed method for delivering therapeutic agent to a body lumen, wherein

FIG. 3 is a schematic cross-sectional representation of the disclosed method of FIG. 2, wherein FIG. 3A is a schematic cross-sectional view of a stenotic arterial blood vessel; FIG. 3B is a schematic cross-sectional view of the same vessel after insertion of the expandable member catheter of FIG. 1; FIG. 3C is a schematic cross-sectional view of the vessel after inflation of the expandable member catheter and intraluminal release of the therapeutic agent and crosslinkable compound; and FIG. 3D is a schematic cross-sectional view of the vessel after inflation of the expandable member catheter with the crosslinkable compound crosslinked on the vessel wall.

DETAILED DESCRIPTION

Figure 2B:
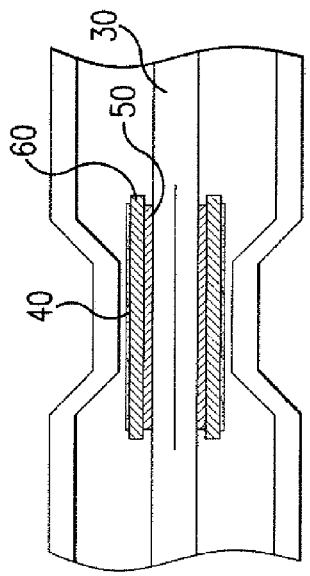
FIG. 2B is a schematic side view of the same vessel after insertion of the expandable member catheter of FIG. 1.

Reference will now be made in detail to embodiments of the disclosed subject matter. The methods and corresponding steps will be described in conjunction with the detailed description of the systems of the disclosed subject matter.

The methods and systems presented herein can be used to deliver a therapeutic agent to a vessel wall of a body lumen. The disclosed subject matter is particularly suited for applying therapeutic agents to a vessel wall of a body lumen in a manner that promotes retention of the therapeutic agent at the site of delivery.

The disclosed subject matter provides a system, and corresponding method, to deliver a therapeutic agent to a vessel wall of a body lumen, whereby the therapeutic agent is retained at the site of delivery by a crosslinkable compound. The delivery systems and corresponding methods deliver a therapeutic agent to the body lumen via an expandable member. The expandable member deposits the therapeutic agent and crosslinkable compound by temporary contact with the vessel wall of the body lumen. The crosslinkable compound is crosslinked after delivery to the body lumen as disclosed herein to promote retention and delivery of the therapeutic agent at the site of delivery.

According to one aspect of the disclosed subject matter, a system for delivering a therapeutic agent to a vessel wall of a body lumen is provided. The system includes an expandable member having a distal end, a proximal end, and a working length therebetween. The expandable member has disposed along at least a portion of its working length a crosslinkable compound for intraluminal release from the expandable member after inflation. The crosslinkable compound of the system is capable of being crosslinked after intraluminal release onto a vessel wall. The expandable member also includes at least one therapeutic agent disposed along a portion of its working length so as to be temporarily retained by the crosslinkable compound after intraluminal release to the vessel wall.

According to another aspect of the claimed invention, a method of delivering a therapeutic agent to a vessel wall of a body lumen is provided. The method includes providing a system including an expandable member having a distal end, a proximal end and a working length therebetween. A crosslinkable compound disposed along at least a portion of the working length of the expandable member, and at least one therapeutic agent disposed along the portion of the working length so as to be temporarily retained by the crosslinkable compound after intraluminal release to the vessel wall. The expandable member is positioned within a body lumen and then expanded to contact the vessel wall for intraluminal release of the crosslinkable compound to the vessel wall. The crosslinkable compound is crosslinked on the vessel wall with the at least one therapeutic agent temporarily retained by the crosslinked compound for delivery to the vessel wall.

Reference will now be made in detail to the various aspects of the disclosed subject matter. The method of the disclosed subject matter will be described in conjunction with the detailed description of the system, the figures and examples provided herein.

Unless otherwise defined, all technical and scientific terms used herein have the same meanings as commonly understood by one of ordinary skill in the art to which the disclosed subject matter belongs. Although methods and materials similar or equivalent to those described herein can be used in its practice, suitable methods and materials are described below.

It is to be noted that the term "a" entity or "an" entity refers to one or more of that entity. As such, the terms "a", "an", "one or more", and "at least one" can be used interchangeably herein. The terms "comprising," "including," and "having" can also be used interchangeably. In addition, the terms "amount" and "level" are also interchangeable and can be used to describe a concentration or a specific quantity. Furthermore, the term "selected from the group consisting of" refers to one or more members of the group in the list that follows, including mixtures (i.e. combinations) of two or more members.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to +/−20%, or up to +/−10%, or up to +/−5%, or up to +/−1% of a given value. Alternatively, particularly with respect to biological systems or processes, the term can mean within an order of magnitude, or within 5-fold, or within 2-fold, of a value. With reference to pharmaceutical compositions, the term "about" refers to a range that is acceptable for quality control standards of a product approved by regulatory authorities.

The systems and methods presented can be used for delivery of a therapeutic agent to a vessel wall of a subject. The methods and systems presented herein can also be used for manufacture and assembly of medical devices such as a drug coated balloon catheter. While the disclosed subject matter references application of a therapeutic agent, it is to be understood that a variety of coatings including polymeric, therapeutic, or matrix coatings, can be applied to various surfaces of medical devices, as so desired.

Referring to FIG. 1, for purposes of illustration and not limitation, an exemplary embodiment of balloon catheter device in accordance with the disclosed subject matter is shown schematically in FIGS. 1A and 1B. As depicted in FIGS. 1A and 1B, the balloon catheter device 10 generally includes an elongated catheter shaft 12 having a proximal end and having a distal end and an expandable member or balloon 30 located proximate to the distal end of the catheter shaft. In accordance with the disclosed subject matter, a crosslinking source 50 is applied to at least a portion of the working length of the balloon catheter. The expandable balloon has an outer surface and an inner surface disposed at the distal end portion of the catheter shaft.

For purpose of illustration and not limitation, an elongated catheter shaft 12 having a coaxial arrangement is shown comprising an outer tubular member 14 and an inner tubular member 16. The outer tubular member 14 defines an inflation lumen 20 disposed between the proximal end portion and the distal end portion of the catheter shaft 12. For example, and as illustrated in FIG. 1B, the coaxial relationship between the inner tubular member 16 and the outer tubular member 14 defines an annular inflation lumen 20. The expandable member 30 is in fluid communication with the inflation lumen 20. The inflation lumen therebetween can supply fluid under pressure to the expandable member 30, and establish negative pressure to draw fluid from the expandable member 30. The expandable member 30 can thus be inflated and deflated. The elongated catheter is sized and configured for delivery through a tortuous anatomy, and can further include a guidewire lumen 22 that permits it to be delivered over a guidewire 18. As illustrated in FIG. 1B, the inner tubular member 16 defines the guidewire lumen 22 for the guidewire 18. Although FIGS. 1A and 1B illustrate the guidewire lumen as having an over-the-wire (OTW) construction, the guidewire lumen can be configured as a rapid-exchange (RX) construction, as is well known in the art. Similarly, the shaft can be provided as a multilumen member, or composition of two or more tubular members, as is known in the art.

As further depicted in FIG. 1A, the expandable member or balloon 30 has a distal end 32, a proximal end 34 and a working length "L" therebetween. The expandable member embodied herein has a an interior chamber 36 in fluid communication with the inflatable lumen 20 of the elongated shaft 12. Any of a number of suitable expandable member constructions and shapes can be used, as described further below.

In accordance with the disclosed subject matter, at least one therapeutic agent 40 is disposed along at least a portion of the working length "L" of the expandable member 30. The at least a portion of the working length can be a selected length of the working length or the working length in its entirety. Furthermore, the at least a portion can reference a pattern on the surface of the working length, such as rings, dots, linear or curvilinear segments, or another design. The at least one therapeutic agent can be disposed along the portion of the working length of the expandable member in any suitable manner that will allow for release from the expandable member to the vessel wall. For example, the at least one therapeutic agent can be applied as a coating to the outer surface of the expandable member. Additionally or alternatively, the expandable member can be provided with reservoirs or similar surface features to contain therapeutic agent for release therefrom. Furthermore, pores or channels can be defined along a portion of the working length for infusion-type release of the therapeutic agent therefrom. The at least one therapeutic agent can be disposed alone, e.g., neat, or in combination with a suitable additive, such as a surfactant, plasticizer or the like. Additionally, and as described further below, the at least one therapeutic agent can be disposed for delivery in combination with a crosslinkable compound 60. For example, the therapeutic agent can be applied as a layer over a layer of the crosslinkable compound, and/or the therapeutic agent can be mixed with the crosslinkable compound as appropriate.

Further in accordance with the disclosed subject matter, a crosslinkable compound is disposed along at least a portion of the expandable member. Upon inflation of the expandable member within the body lumen, the crosslinkable compound is transferred from the outer surface of the expandable member to the wall of the lumen. In this manner, upon or after transfer from the expandable member to the body lumen, the crosslinkable compound can be crosslinked to retain the therapeutic agent at the site of delivery. As with the therapeutic agent, as disclosed in further detail below, the crosslinkable compound can be disposed along the portion of the working length in a variety of suitable manners. For example, and not limitation, the crosslinkable compound can be applied as a coating on an outer surface of the expandable member, and/or can be confined in reservoirs or the like defined in the outer surface. Furthermore, the crosslinkable compound can be disposed for delivery from the expandable member through pores, channels or the like defined thereon.

Additionally, and as depicted schematically in FIG. 1, a crosslinking source 50 can be provided to crosslink the crosslinkable compound 60 after delivery or release from the expandable member onto the vessel wall if needed. The crosslinking source 50 will depend on the crosslinkable compound 60 to be used, as described further below. Examples of such crosslinking sources can include, but are not limited to, heat source, light source and/or independent source of delivering a solvent or crosslinking agent, as described further below. Although the crosslinking source 50 depicted herein is provided on the expandable member used for delivery of the therapeutic agent 40 and/or crosslinkable compound 60, it is recognized that the crosslinking source 50 can be provided spaced from the expandable member, or can be provided on a separate catheter as desired or appropriate.

Reference is now made to various crosslinking compounds, dispositions, techniques and crosslinking sources. It is understood that such examples can be combined and/or interchanged as desired and appropriate.

For purpose of illustration and not limitation, the crosslinkable compound can be disposed as a coating on the outer surface of the expandable member. As noted above, the coating of the expandable member can further include an outer layer containing at least one therapeutic agent. Additionally or alternatively, the therapeutic agent can be combined or mixed with the crosslinkable compound as a coating on the outer surface of the expandable member. Upon inflation of the expandable member, the coating containing the at least one therapeutic agent is transferred to the wall of the body lumen. If the therapeutic agent is disposed as a separate outer layer, then the crosslinkable compound is disposed over the therapeutic agent on the vessel wall. The crosslinkable compound is subsequently crosslinked to temporarily retain the therapeutic agent at the site of delivery. The site of delivery can be, for example, a stenotic lesion, although the site can be any suitable body lumen where delivery of a therapeutic agent is desired.

Figure 2D:
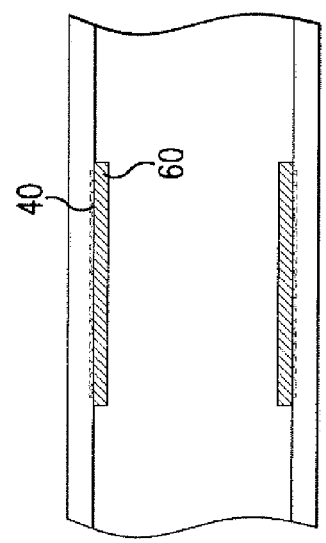
FIG. 2D is a schematic side view of the vessel after inflation of the expandable member catheter with the crosslinkable compound crosslinked on the vessel wall.
Figure 2A:
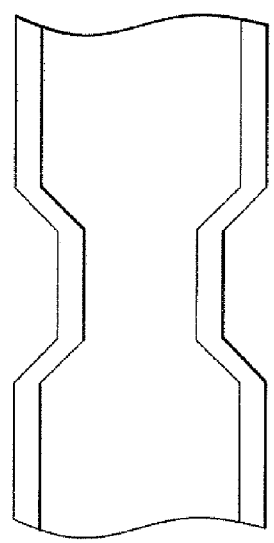
FIG. 2A is a schematic side view of a stenotic arterial blood vessel.
Figure 2C:
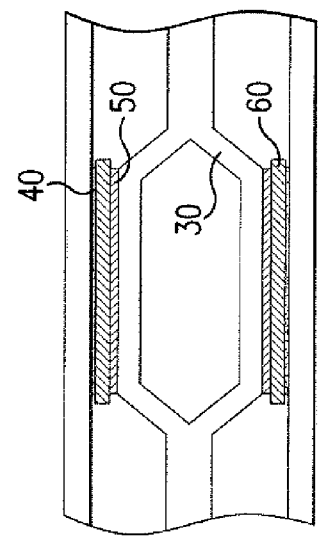
FIG. 2C is a schematic side view of the vessel after inflation of the expandable member catheter and intraluminal release of the therapeutic agent and crosslinkable compound.

This process is illustrated schematically for purpose of understanding and not limitation in FIG. 2 and FIG. 3. FIGS. 2A and 3A show a stenotic arterial vessel. An expandable member 30 according to the present invention is introduced as shown in FIGS. 2B and 3B. The expandable member 30 is expanded as shown in FIGS. 2C and 3C to deliver the therapeutic agent 40 and crosslinkable compound 60 to the vessel wall. Particularly, and with reference to the embodiments above having an outer layer of therapeutic agent and underlying layer of crosslinkable compound, the therapeutic agent 40 is transferred to the vessel wall and the crosslinkable compound 60 is disposed over the therapeutic agent on the vessel wall. The crosslinkable compound 60 can then be crosslinked using a suitable crosslinking source 50 either disposed on the expandable member or on a separate catheter as desired. As depicted in FIGS. 2D and 3D, the crosslinkable compound 60 is thus retained on the vessel wall after removal of the expandable member, and the therapeutic agent 40 can then be absorbed at the site of delivery.

Although reference is made above to the use of a coating on the expandable member, additional and/or alternative techniques can be used to dispose the therapeutic agent and/or crosslinking compound along a portion of the working length. For example, and as embodied herein, the expandable member can have an outer surface with reservoirs or similar features defined along a portion of the working length of the member. The crosslinkable compound thus can be disposed for intraluminal release within the reservoirs. Upon inflation of the expandable member, the crosslinkable compound and/or at least one therapeutic agent is released from the reservoirs and transferred to the vessel wall of the body lumen. For example, the crosslinking compound can be disposed in a first set of reservoirs and the therapeutic agent can be disposed in a second set of reservoirs. Alternatively, the crosslinking compound can be mixed with or disposed as a first layer within the reservoirs and the therapeutic agent can be disposed as a second layer within the same reservoirs as the crosslinking compound.

Additionally or alternatively, an infusion technique can be used for delivery of the crosslinking compound and/or therapeutic agent. For example, the expandable member can have pores or channels defined therein along a portion of the working length, wherein the crosslinkable compound and/or at least one therapeutic agent is disposed for intraluminal release through the pores. Upon inflation of the expandable member, the crosslinkable compound and/or at least one therapeutic agent can be extruded or otherwise released through the pores or channels and transferred to vessel wall of the body lumen. The crosslinking compound and therapeutic agent can be disposed for release through separate pores, or mixed for delivery together through the same pores.

It will be appreciated by those skilled in the art that the at least one therapeutic agent can be delivered in combination with the crosslinking compound, wherein the therapeutic agent or agents is trapped within the crosslinked compound after crosslinking. The therapeutic agent or agents thus can be released over time into the vessel wall as desired. Additionally or alternatively, the therapeutic agent or agents can be delivered according to the exemplary embodiments provided so as to be confined against or forced into the vessel wall by the crosslinked material.

In accordance with the disclosed subject matter, the crosslinkable compound can be crosslinkable by thermal treatment. "Thermal treatment" generally refers to the transfer of thermal energy from an extrinsic or intrinsic source to the crosslinkable compound. Suitable compounds crosslinkable by thermal treatment include, but are not limited to, silk-elastin-like protein-based polymers, pluronics F127, pluronics F68, poly-NIPAAM, poly-NIPAAM-co-acrylic acid, PEG-PEG-PLA-PEG, PLGA-PEG,PLGA, solubilized extracellular matrix, self-assembling peptides, hydroxypropylmethylcellulose, and a combination thereof. Such thermally crosslinkable compounds generally can crosslink at or above about 37 degrees Celsius, such as by a heat source disposed on or proximate the expandable member.

Such thermally crosslinkable compounds are advantageous in that only one compound is required for crosslinking, although additional additives or potentially reactive compounds can be used but are necessarily required. With regard to the non-limiting example of silk-elastin like protein polymer, the crosslinkable compound is delivered by, for example, one of the exemplary techniques above, and subsequently crosslinked at the site of delivery by thermal filaments or other suitable heat source on the expandable member to crystallize irreversibly to a β-sheet configuration. Such a stable crosslinked configuration provides improved retention of the crosslinkable compound and therapeutic agent(s) upon the vessel wall. With regard to another non-limiting example of Pluronics F127, the crosslinkable compound can be a liquid at room temperature and gelate at body temperature. Upon catheter delivery and inflation, gelation at body temperature permits retention of the compound at the site of delivery.

In accordance with additional embodiments of the disclosed subject matter, the crosslinkable compound can be crosslinked by melt thermal treatment. "Melt thermal treatment" as used herein generally refers to heat melting of a polymer in vivo or ex vivo. Suitable melt thermal polymers subsequently crosslink as they re-solidify. Melt thermal crosslinkable compounds include but are not limited to poly (ε-caprolactone), poly(ortho esters), polyanhrydrides, and combinations thereof. Such melt thermal crosslinkable compounds can crosslink at or below about 37 degrees Celsius. As embodied herein, the crosslinking source for such melt thermal crosslinkable compounds can include a heat source to heat the melt thermal crosslinkable compound to a temperature above about 37 degrees Celsius prior to delivery and release from the expandable member. In this manner, and with reference to the non-limiting example of Poly(ε-caprolactone), the crosslinkable compound can be delivered in the form of a polymer melt above a $T_m$ of about 60 degrees Celsius or heated in situ to a temperature above about 60 degrees Celsius. After release from the expandable member onto the vessel wall, the crosslinkable compound then solidifies at body temperature and crosslinks to permit retention of the compound at the site of delivery.

In yet other embodiments in accordance with the disclosed subject matter, the crosslinkable compound is crosslinked by photoactivation. "Photoactivation" as used herein generally refers to the application of light or electromagnetic energy of a suitable wavelength and intensity, such as the visible or ultraviolet portion of the electromagnetic spectrum, to the crosslinkable compound during or after delivery. Suitable crosslinkable compounds capable of being crosslinked by photoactivation include, but are not limited to, PEG diacrylate and 2-hydroxy-1-[4-(hydroxyethoxy)phenyl]-2-methyl-1-propanone (Irgacure 2959®). Suitable photoactivators for such compounds include, but are not limited to, ultraviolet light. Where the crosslinkable compound is crosslinked by photoactivation, the crosslinking source is provided as a light source as a component of the catheter assembly, or as a separate catheter component.

In other embodiments in accordance with the disclosed subject matter, the crosslinkable compound is crosslinked by solvation. "Solvation" as used herein generally refers to the introduction or application of solvent to the crosslinkable compound before, during, or after delivery. Suitable crosslinkable compounds which are crosslinked by solvation include but are not limited to poly(ester amide) ("PEA"), PLGA, PDLLA, PLLA, PLGA-PEG-PLGA, PLLA-PEG-PLLA, N-methylpyrrolidinone, dimethyl sulfoxide, dicholoromethane, and a combination thereof. Such compounds readily dissolve hydrophobic drugs and therefore can be advantageous in certain indications. By solvation of the crosslinkable compound with drug-loaded solvent, a crosslinked formulation incorporating the desired hydrophobic drug(s) can be formed at the site of balloon inflation. By way of example and not limitation, according to certain exemplary embodiments of the present invention, PEA can be delivered to the vessel wall of the body lumen in accordance with a delivery system described herein, and crosslinked by solvation using N-methylpyrrolidinone to form a crosslinked formulation retained on the vessel wall at the site of delivery. In this exemplary embodiment, the crosslinking source can be one or more pores for the release of the solvent into or in combination with the crosslinkable compound.

In yet other embodiments in accordance with the disclosed subject matter, the crosslinkable compound provided is shear-sensitive so as to crosslink upon removal of shear stress. For example, removal of shear stress can occur upon intraluminal release of the crosslinkable compound to the vessel wall. Suitable shear-sensitive crosslinkable compounds include but are not limited to sodium hyaluronate (for example, Healon5®) and sodium alginate, as well as certain lightly crosslinked hydrogels such as lightly crosslinked sodium alginate and sodium hyaluronate methylcellulose blends, and combinations thereof. These compounds gelate immediately upon removal of shear and thus can be retained on the vessel wall at the site of delivery. Where light crosslinking is desired before delivery, such preliminary crosslinking can be effected prior to incorporation of the lightly crosslinked compounds into the systems provided, rather than in vivo.

In other embodiments in accordance with the disclosed subject matter, the crosslinkable compound can be selected to crosslink when exposed to an environment within a pH range of about 6.8 to about 7.4. Suitable crosslinkable compounds that crosslink within a pH range of about 6.8 to about 7.4 include, but are not limited to, acid-soluble collagen, chitosan, polyacrylic acid and combinations thereof. By way of example, and not limitation, acidic recombinant collagen can be delivered to the vessel wall of the body lumen according to the embodiments provided herein. Upon contact with the neutral body pH of the vessel wall, the acidic collagen solution neutralizes and gelates, with the therapeutic agent(s) captured therein. The gelated collagen solution is retained on the vessel wall at the site of delivery with the therapeutic agent(s) captured therein.

In yet other embodiments in accordance with the disclosed subject matter, the crosslinkable compound is crosslinked by chemical reaction with one or more additional compounds. The additional compound(s) can be selected to be chemically reactive with the first crosslinkable compound. These additional compounds can be disposed along and/or released from at least a portion of the working length of the expandable member. By way of example, the additional compounds can be disposed in a top coating layer or a base layer. Additionally or alternatively, the additional compound(s) can be released from reservoirs or pores defined in the expandable member, similar to the solvent described above. Upon inflation of the expandable member and compression of the coating against the vessel wall, the crosslinkable compound and additional compound or compounds are mechanically mixed to promote crosslinking of the mixture on the vessel wall. Alternatively, the additional compound may be delivered via a second expandable balloon or via reservoirs or channels in the first balloon.

By way of example, and as described below, chemically crosslinkable compounds for delivery by a balloon to temporarily retain one or more therapeutic agents include hydrophilic polymers, peptide hydrogels, carbohydrate hydrogels, and combinations thereof. Suitable hydrophilic polymers for chemical crosslinking include, but are not limited to, polyethylene glycol ("PEG"), PLLA-PEG-PLLA copolymers, PLDA-PEG-PLDA copolymers, PLGA-PEG-PLGA copolymers, PEG-PLLA copolymers, PEG-PLDA copolymers, PEG-PLGA copolymers, and combinations thereof. Suitable peptide and carbohydrate hydrogel components for chemical crosslinking include alginate, hyaluronic acid, collagen, laminin, poly-l-lysine, fibrin, fibrinogen, gelatin, and combinations thereof.

Additionally, the hydrophilic polymers, peptide and carbohydrate hydrogel components, and can be functionalized with reactive functional groups to promote chemical crosslinking. Suitable functional groups include, without limitation, thiol, vinyl, amino, acrylate, methacrylate, aldehyde, vinylsulfone, succinimidyl, hydroxysuccinimidyl, nitrophenolate, and carbohydrazide moieties. According to some embodiments of the disclosed subject matter, the crosslinkable compound is functionalized with reactive functional groups. In additional embodiments, both the crosslinkable compound and the additional compound or compounds are functionalized with reactive functional groups. In still further embodiments, only the additional compound or compounds are functionalized with reactive functional groups.

In some embodiments of the disclosed subject matter, the crosslinkable compound is crosslinked by a Micheal's addition reaction. For example, the crosslinkable compound can be functionalized with a nucleophile, and the additional compound functionalized with an electrophile. When the crosslinkable compound and the additional compound come into contact with one another, e.g., by infusion from pores and/or upon mechanical mixing by balloon inflation as described above, a Micheal's addition reaction occurs in situ between the nucleophilic compound and the electrophilic compound to form a crosslinked composite on the vessel wall at the site of balloon inflation. Michael's reactions proceed relatively quickly, on the order of seconds to hours, and accordingly are well-suited to crosslinking in situ to retain therapeutic agent at the vessel wall.

In additional embodiments, the crosslinkable compound can be crosslinked by the formation of disulfide bonds in an oxidative reaction. For example, the crosslinkable compound may be functionalized with thiol residues which form disulfide bonds in oxidizing conditions. The additional compound can be an oxidizing compound to promote disulfide bond formation in situ.

The additional compound or compounds is selected to be chemically reactive with the first crosslinkable compound in an environment having a predetermined pH, which in certain embodiments is at least about 6.8. In some embodiments, including but not limited to those in which a relatively rapid rate of crosslinking is desired, an additional compound can be provided to activate the reactive functional groups. By way of example and not litigation, a basic buffer can be provided in reservoirs on the balloon or channels in the balloon to accelerate crosslinking of the crosslinkable compound by initiating deprotonation of nucleophilic functional groups. In certain embodiments, this buffer has a pH between about 7.0 and about 10.0.

By way of example and not limitation, according to certain embodiments of the disclosed subject matter, the crosslinkable compound is a PEG polymer comprised of multi-arm PEG monomers wherein each PEG arm is functionalized with a nucleophilic functional group. An additional compound is provided consisting of a PEG polymer comprised of multi-arm PEG monomers wherein each PEG arm is functionalized with an electrophilic functional group. By way of example, suitable nucleophilic functional groups include, without limitation, thiol, amino, hydroxyl, and CO—NH_NH2 groups, while suitable electrophilic functional groups include, without limitation, acrylate, vinylsulfone, and N-hydroxysuccinimide groups. In some embodiments, the inter-polymer crosslinking chemical reaction results in the formation of biodegradable covalent bonds, such as ester linkages. For example, the reaction of PEG-acrylate and PEG-thiol results in the formation of thioester bonds, which are readily hydrolyzed in vivo.

In some embodiments, the multi-arm PEG crosslinkable compound has between 1 and 16 arms, and has a linear, comb, branched or star configuration. The PEG crosslinkable compound can also have a molecular weight of between about 2 and 40 kDa. In additional embodiments, the additional multi-arm PEG crosslinkable compound has between 1 and 16 arms, has a linear, comb, branched or star configuration, and has a molecular weight of between 2 and 40 kDa.

In further embodiments, the crosslinkable compound is a multi-arm PEG as described above, while the additional compound is a peptide or carbohydrate polymer. In one such exemplary embodiment, PEG-NHS ester is delivered to the body lumen as a crosslinkable compound, and gelatin is provided as an additional compound. Gelatin is, for example, disposed along the expandable member, and chemically reacts with the PEG-NHS ester to gelate in situ to promote temporary retention of the crosslinkable compound at the site of delivery. In further embodiments, the crosslinkable compound is a carbohydrate functionalized with reactive functional groups. By way of example and not limitation, the crosslinkable carbohydrate compound can be sodium hyaluronate acrylate, hyaluronate-thiol, or methacrylate-modified alginate.

In other embodiments in accordance with the disclosed subject matter, the crosslinkable compound provided is crosslinked by ionic crosslinking. For example, a second compound can be provided to effect ionic crosslinking of the crosslinkable compound, and can be disposed along a portion of the working length of the expandable member. Suitable crosslinkable compounds which are crosslinked by ionic crosslinking include but are not limited to sodium alginate, pectin, aloe pectin, alginate conjugates, including alginate-collagen and alginate laminin, and combinations thereof. Suitable second compounds for ionic crosslinking include but are not limited to calcium chloride, barium chloride, calcium chloride and combinations thereof. In this manner, and as with the solvent embodiments above, the separate compounds can be delivered as separate layers and/or by infusion through separate pores, and the mechanically mixed upon inflation, or by separate expandable members.

A variety of suitable therapeutic agents can be delivered by the systems and methods disclosed herein. In accordance with the disclosed subject matter, and for purpose of illustration and not limitation, the therapeutic agent or drug can include any of a variety of suitable anti-proliferative, anti-inflammatory, anti-neoplastic, anti-platelet, anti-coagulant, anti-fibrin, anti-thrombotic, anti-mitotic, antibiotic, anti-allergic and antioxidant compounds. Thus, the therapeutic agent can be, again without limitation, a synthetic inorganic or organic compound, a protein, a peptide, a polysaccharides and other sugars, a lipid, DNA and RNA nucleic acid sequences, an antisense oligonucleotide, an antibody, a receptor ligands, an enzyme, an adhesion peptide, a blood clot agent including streptokinase and tissue plasminogen activator, an antigen, a hormone, a growth factor, a ribozyme, and a retroviral vector.

The term "anti-proliferative" as used herein means an agent used to inhibit cell growth, such as chemotherapeutic drugs. Some non-limiting examples of anti-proliferative drugs include taxanes, paclitaxel, docetaxel, and protaxel. Anti-proliferative agents can be anti-mitotic. The term "anti-mitotic" as used herein means an agent used to inhibit or affect cell division, whereby processes normally involved in cell division do not take place. One sub-class of anti-mitotic agents includes vinca alkaloids. Representative examples of vinca alkaloids include, but are not limited to, vincristine, paclitaxel, etoposide, nocodazole, indirubin, and anthracycline derivatives, including, for example, daunorubicin, daunomycin, and plicamycin. Other sub-classes of anti-mitotic agents include anti-mitotic alkylating agents, including, for example, tauromustine, bofumustine, and fotemustine, and anti-mitotic metabolites, including, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing. An example of an anti-mitotic agent includes, but is not limited to, paclitaxel. As used herein, paclitaxel includes the alkaloid itself and naturally occurring forms and derivatives thereof, as well as synthetic and semi-synthetic forms thereof.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, including, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpI-IbIIIa or avb3, antibodies that block binding to gpIIaIIIb or avb3, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

As discussed above, at least one therapeutic agent can be an anti-inflammatory agent. Non-limiting examples of anti-inflammatory agents include prednisone, dexamethasone, dexamethasone acetate, hydrocortisone, estradiol, triamcinolone, mometasone, fluticasone, clobetasol, and non-steroidal anti-inflammatories, including, for example, acetaminophen, ibuprofen, naproxen, adalimumab and sulindac. The arachidonate metabolite prostacyclin or prostacyclin analogs is an example of a vasoactive antiproliferative. Other examples of these agents include those that block cytokine activity or inhibit binding of cytokines or chemokines to the cognate receptors to inhibit pro-inflammatory signals transduced by the cytokines or the chemokines. Representative examples of these agents include, but are not limited to, anti-IL1, anti-IL2, anti-IL3, anti-IL4, anti-IL8, anti-IL15, anti-IL18, anti-MCP1, anti-CCR2, anti-GM-CSF, and anti-TNF antibodies.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, including, for example, heparin, heparin sulfate, low molecular weight heparins, including, for example, the compound having the trademark Clivarin®, and synthetic oligosaccharides, including, for example, the compound having the trademark Arixtra®. Also included are direct thrombin inhibitors, including, for example, melagatran, ximelagatran, argatroban, inogatran, and peptidomimetics of binding site of the Phe-Pro-Arg fibrinogen substrate for thrombin. Another class of antithrombotic agents that can be delivered is factor VII/VIIa inhibitors, including, for example, anti-factor VII/VIIa antibodies, rNAPc2, and tissue factor pathway inhibitor (TFPI).

Thrombolytic agents, which can be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

Furthermore, the therapeutic agents include a cytostatic agent. The term "cytostatic" as used herein means an agent that mitigates cell proliferation, allows cell migration, and does not induce cell toxicity. These cytostatic agents include, for the purpose of illustration and without limitation, macrolide antibiotics, zotarolimus, sirolimus, rapamycin, everolimus, biolimus, myolimus, novolimus, temsirolimus, deforolimus, merilimus, sirolimus derivatives, tacrolimus, pimecrolimus, derivatives and analogues thereof, any macrolide immunosuppressive drugs, and combinations thereof. Other therapeutic agents include cytotoxic drugs, including, for example, apoptosis inducers, including TGF, and topoisomerase inhibitors, including, 10-hydroxycamptothecin, irinotecan, and doxorubicin.

Examples of anti-inflammatory drugs include both steroidal and non-steroidal anti-inflammatories (NSAID) such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclopro-fen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexmethasone phosphate, momentasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimex-olone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus and pimecrolimus.

Additionally or alternatively, the agent can include other compounds or additives, such as excipients, binding agents, plasticizers, solvents, surfactants, additives, fillers, and the like. Examples of possible compounds include polyvinylpyrrolidone, gelatin, maltrodextrin, starch, hydroxypropyl methyl cellulose, glycerol, polyethylene glycol, polysorbates, tweens, polyoxamers, Vitamin E tocopheryl polyethylene glycol succinate ("TPGS"), fatty alcohols, fatty esters, tocopherols, and phospholipids. In some embodiments, these additives can be selected to tune the dissolution rate of the crosslinked compound after crosslinking as desired. In one embodiment, the therapeutic agent can be provided in liquid form or dissolved in a suitable solvent. In further embodiments, therapeutic agent is provided as a particulate and mixed in a suitable carrier for application as a fluid.

While the disclosed subject matter is described herein in terms of certain exemplary embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

A wide variety of balloon catheters and balloon constructs are known and suitable for use in accordance with the disclosed subject matter. For purpose of illustration and not limitation, the expandable member is fabricated from polymeric material such as compliant, non-compliant or semi-compliant polymeric material or polymeric blends (e.g., a mixture of polymers). In one embodiment, the polymeric material is compliant such as but not limited to a polyamide/polyether block copolymer (commonly referred to as PEBA or polyether-block-amide). In some embodiments, the polyamide and polyether segments of the block copolymers can be linked through amide or ester linkages. The polyamide block can be selected from various aliphatic or aromatic polyamides known in the art. In some embodiments, the polyamide is aliphatic. Some non-limiting examples include nylon 12, nylon 11, nylon 9, nylon 6, nylon 6/12, nylon 6/11, nylon 6/9, and nylon 6/6. In some embodiments, the polyamide is nylon 12. The polyether block can be selected from various polyethers known in the art. Some non-limiting examples of polyether segments include poly(tetramethylene ether), tetramethylene ether, polyethylene glycol, polypropylene glycol, poly(pentamethylene ether) and poly(hexamethylene ether). Commercially available PEBA material can also be utilized such as for example, PEBAX® materials supplied by Arkema (France). Various techniques for forming a balloon from polyamide/polyether block copolymer is known in the art. One such example is disclosed in U.S. Pat. No. 6,406,457 to Wang, the disclosure of which is incorporated by reference.

In additional embodiments, the balloon material is formed from polyamides. In some embodiments, the polyamide has substantial tensile strength, be resistant to pin-holing even after folding and unfolding, and be generally scratch resistant, such as those disclosed in U.S. Pat. No. 6,500,148 to Pinchuk, the disclosure of which is incorporated herein by reference. Some non-limiting examples of polyamide materials suitable for the balloon include nylon 12, nylon 11, nylon 9, nylon 69 and nylon 66. In some embodiments, the polyamide is nylon 12. Other suitable materials for constructing non-compliant balloons are polyesters such as poly(ethylene terephthalate) (PET), Hytrel thermoplastic polyester, and polyethylene.

In additional embodiments, the balloon is formed of a polyurethane material, such as TECOTHANE® (Thermedics). TECOTHANE® is a thermoplastic, aromatic, polyether polyurethane synthesized from methylene disocyanate (MDI), polytetramethylene ether glycol (PTMEG) and 1,4 butanediol chain extender. TECOTHANE® grade 1065D is suitable, and has a Shore durometer of 65D, an elongation at break of about 300%, and a high tensile strength at yield of about 10,000 psi. However, other suitable grades can be used, including TECOTHANE® 1075D, having a Shore D hardness of 75. Other suitable compliant polymeric materials include ENGAGE® (DuPont Dow Elastomers (an ethylene alpha-olefin polymer) and EXACT® (Exxon Chemical), both of which are thermoplastic polymers. Other suitable compliant materials include, but are not limited to, elastomeric silicones, latexes, and urethanes.

The compliant material can be cross linked or uncrosslinked, depending upon the balloon material and characteristics required for a particular application. Certain polyurethane balloon materials are not crosslinked. However, other suitable materials, such as the polyolefinic polymers ENGAGE® and EXACT®, can be crosslinked. By crosslinking the balloon compliant material, the final inflated balloon size can be controlled. Conventional crosslinking techniques can be used including thermal treatment and E-beam exposure. After crosslinking, initial pressurization, inflation, and preshrinking, the balloon will thereafter expand in a controlled manner to a reproducible diameter in response to a given inflation pressure, and thereby avoid overexpanding the stent (if used in a stent delivery system) to an undesirably large diameter.

In one embodiment, the balloon is formed from a low tensile set polymer such as a silicone-polyurethane copolymer. In some embodiments, the silicone-polyurethane is an ether urethane and more specifically an aliphatic ether urethane such as PURSIL AL 575A and PURSIL AL10, (Polymer Technology Group), and ELAST-EON 3-70A, (Elastomedics), which are silicone polyether urethane copolymers, and more specifically, aliphatic ether urethane cosiloxanes. In an alternative embodiment, the low tensile set polymer is a diene polymer. A variety of suitable diene polymers can be used such as but not limited to an isoprene such as an AB and ABA poly(styrene-block-isoprene), a neoprene, an AB and ABA poly(styrene-block-butadiene) such as styrene butadiene styrene (SBS) and styrene butadiene rubber (SBR), and 1,4-polybutadiene. In some embodiments, the diene polymer is an isoprene including isoprene copolymers and isoprene block copolymers such as poly(styrene-block-isoprene). A suitable isoprene is a styrene-isoprene-styrene block copolymer, such as Kraton 1161K available from Kraton, Inc. However, a variety of suitable isoprenes can be used including HT 200 available from Apex Medical, Kraton R 310 available from Kraton, and isoprene (i.e., 2-methyl-1,3-butadiene) available from Dupont Elastomers. Neoprene grades useful in the disclosed subject matter include HT 501 available from Apex Medical, and neoprene (i.e., polychloroprene) available from Dupont Elastomers, including Neoprene G, W, T and A types available from Dupont Elastomers.

In accordance with another aspect of the disclosed subject matter, the outer surface of the balloon is modified. In this regard, the balloon surface can include a textured surface, roughened surface, voids, spines, channels, dimples, pores, or microcapsules or a combination thereof, as will be described below.

In further embodiments of the disclosed subject matter, the balloon is formed of a porous elastomeric material having at least one void formed in the wall of the balloon surface. For example, the entire cross section of the balloon can contain a plurality of voids. Alternatively, the plurality of void can be distributed along select lengths of the balloon outer surface. For example and not limitation, the plurality of voids can be distributed only along the working section of the balloon. The voids define an open space within the outer surface of the balloon. In some embodiments, the crosslinkable compound and/or therapeutic agent is dispersed within the space defined by the plurality of voids across the cross section of the balloon outer surface.

In operation, the therapeutic agent, crosslinkable compound, or crosslinking source is released or is expelled from the pores upon inflation of the balloon. In this regard, the durometer of the polymeric material of the balloon surface and in particular the depression of the void is sufficiently flexible to allow for expulsion of the therapeutic agent and/or coating contained within the plurality of voids upon inflation of the balloon. The expelled coating with therapeutic agent is released into the vessel lumen or into the tissue surrounding and contacting the inflated balloon.

In alternative embodiments, the balloon can include two concentric balloons in a nesting configuration. In certain embodiments, the crosslinkable compound and/or therapeutic agent is disposed between the two concentric balloons. Alternatively, a crosslinking catalyst is disposed between the two concentric balloons. Thus, the space between the two concentric balloons; one being an interior balloon and the other being an exterior balloon, acts as a reservoir. In this regard, the protrusions can include apertures for expulsion of the crosslinking source, such as a solvent or crosslinking agent as disclosed above, or expulsion of the crosslinkable compound and/or therapeutic agent upon inflation of the interior and exterior concentric balloons. For example, as described in U.S. Pat. No. 6,991,617 to Hektner, the disclosure of which is incorporated herein by reference thereto. In another embodiment, the balloon can include longitudinal protrusions configured to form ridges on the balloon surface. As described in U.S. Pat. No. 7,273,417 to Wang, the entire disclosure of which is incorporated herein by reference, the ridges can be formed of filaments spaced equidistantly apart around the circumference of the balloon. However, a larger or smaller number of ridges can alternatively be used. The longitudinal ridges can be fully or partially enveloped by the polymeric material of the balloon.

In still further embodiments of the disclosed subject matter, the balloon can include microcapsules on its outer surface. In this regard, the microcapsules are configured to encompass the crosslinking source and/or the crosslinkable compound and/or therapeutic agent. Upon inflation of the balloon the microcapsules located on the surface of the balloon contact the tissue of the arterial wall. Alternatively, the microcapsules can be formed in the wall of the balloon surface. The crosslinkable compound and/or therapeutic agent can be released from the microcapsules by fracturing of the microcapsules and/or diffusion from the microcapsule into the arterial wall. The microcapsules can be fabricated in accordance with the methods disclosed in U.S. Pat. No. 5,1023,402 to Dror or U.S. Pat. No. 6,129,705 to Grantz and the patents referenced therein, each of which is incorporated herein by reference in its entirety.

In additional embodiments in accordance with the disclosed subject matter, the surface of the expandable member or balloon is modified to promote deposition of the crosslinking source and/or the crosslinkable compound and/or the therapeutic agent on the balloon surface and within the balloon wall membrane. Suitable techniques for such modification are disclosed, for example, in U.S. Patent Publication No. 2008/0113081 to Hosseiny et al., hereby incorporated by reference in its entirety.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A system to deliver a therapeutic agent to a vessel wall of a body lumen, comprising:
   (a) an expandable member having a distal end, a proximal end and a working length there between;
   (b) a first compound disposed along at least a portion of the working length for intraluminal release therefrom after inflation of the expandable member;
   (c) a second compound disposed along the portion of the working length of the expandable member, the second compound capable of crosslinking with the first compound; and
   (d) at least one therapeutic agent disposed along the portion of the working length;
   wherein at least one of the first compound and the second compound is a hydrophilic polymer functionalized with reactive functional groups,
   wherein the first compound and the second compound are configured to crosslink with each other upon inflation of the expandable member against a vessel wall to temporarily retain the therapeutic agent at the vessel wall, and
   wherein the functional groups are selected from the group consisting of hydroxyl, carbohydrazide, NHS, acrylate, methacrytate, amine, thiol, and vinylsulfone groups, and combinations thereof.

2. The system of claim 1, wherein the first compound is disposed as a coating layer on the expandable member.

3. The system of claim 1, wherein the expandable member has an outer surface with reservoirs or pores defined therein along the portion of the working length, the second compound being disposed for intraluminal release from the reservoirs or pores.

4. The system of claim 1, wherein the at least one therapeutic agent is combined with the first compound.

5. The system of claim 1, wherein the first compound and the second compound are selected to be chemically reactive in an environment having a pH of at least 6.8.

6. The system of claim 2, wherein the first compound is disposed as a base layer coating on the expandable member and the second compound is disposed as a coating layer over the base layer coating.

7. The system of claim 3, further comprising a basic buffer disposed for intraluminal release within the reservoirs.

8. The system of claim 5, wherein at least one of the first compound and the second compound is selected from the group consisting of PEG, copolymers of PLLA and PEG, copolymers of PLDA and PEG, copolymers of PLGA and PEG, copolymers of PEG, PLLA, and PLDA, copolymers of PEG, PLLA and PLGA, copolymers of PEG, PLDA and PLGA, and combinations thereof.

9. The system of claim 1, wherein the first compound is PEG and the second compound is selected from the group consisting of PEG, a peptide hydrogel, and a carbohydrate hydrogel, optionally wherein the peptide hydrogel is selected from the group consisting of collagen, laminin, poly-l-lysine, fibrin, fibrinogen, gelatin, and combinations thereof, or the carbohydrate hydrogel is selected from the group consisting of alginate, hyaluronic acid, and combinations thereof.

10. The system of claim 1, wherein each of the first compound and the second compound is a hydrophilic polymer functionalized with reactive functional groups.

* * * * *